United States Patent [19]

Carlon et al.

[11] Patent Number: 5,059,352
[45] Date of Patent: Oct. 22, 1991

[54] METHOD FOR THE GENERATION OF MONODISPERSED AEROSOLS FOR FILTER TESTING

[75] Inventors: Hugh R. Carlon, Fallston; Mark A. Guelta, White Marsh; Bernard V. Gerber, Havre de Grace. all of Md.

[73] Assignee: The United States of America as represented by the Secretary of the Army, Washington, D.C.

[21] Appl. No.: 636,159

[22] Filed: Dec. 31, 1990

[51] Int. Cl.$^5$ .............................................. C09F 7/00
[52] U.S. Cl. ............................... 252/408.1; 252/305; 356/336; 73/40
[58] Field of Search ............................ 252/408.1, 305; 356/336; 73/40

[56] References Cited

U.S. PATENT DOCUMENTS

| | | | |
|---|---|---|---|
| H267 | 5/1987 | Carlton et al. | 356/336 |
| 4,914,957 | 4/1990 | Dougherty | 73/40 |
| 4,917,830 | 4/1990 | Ortiz et al. | 261/18.1 |
| 4,963,289 | 10/1990 | Ortiz et al. | 252/305 |

Primary Examiner—Robert L. Stoll
Assistant Examiner—Nina Bhat
Attorney, Agent, or Firm—Anthony T. Lane; Edward Goldberg; Edward F. Costigan

[57] ABSTRACT

An improved method of testing a particulate filter. This is accomplished by passing a salt nucleus coated with a composition containing a poly-alpha olefin having chain length in %, by volume, of about 97-99% of 20 carbon atoms, and about 3% of 30 carbon atoms.

4 Claims, 2 Drawing Sheets

AIR FLOW DIAGRAM - PROTOTYPE PENETROMETER

FIG. 1 AIR FLOW DIAGRAM - PROTOTYPE PENETROMETER

METHOD FOR THE GENERATION OF MONODISPERSED AEROSOLS FOR FILTER TESTING

GOVERNMENTAL INTEREST

The invention described herein may be made, used or licensed by or for the Government for governmental purposes without the payment to us of any royalties thereon.

FIELD OF USE

An improved method of testing a filter for gas masks, respirators, and other personal protective equipment.

BACKGROUND OF THE INVENTION

The present invention relates to a method for the generation of a nearly monodispersed aerosol in a filter-testing penetrometer machine.

The present invention is superior to the previous method in that it employs an composition as a replacement for dioctyl phthalate, which is a suspected carcinogen. The composition utilized in this invention is manufactured by Henkel Corporation, Emery Group, 11501 Northlake Drive, P. O. Box 429557, Cincinnati, OH 45249. The composition has been identified as a thermally stable material of low toxicity. The composition is a poly-alpha olefin containing about 97-99% by volume of a poly-alpha olefin having a chain length of 20 carbon atoms and about 1-3% by volume of a poly-alpha olefin having a chain length of 30 carbon atoms. The term poly-alpha olefin in this case is also called a synthetic hydrocarbon 2 CST fluid. The CST refers to centistokes, a measure of viscosity. The number ahead of the CST fluid specifies the viscosity at 100%.

Recently, a new generation of smoke penetrometers has been developed which utilize the generation of cold smokes or cold aerosols. Cold smokes or aerosols can be generated by the process of cold atomization/vaporization, and controlled nucleated recondensation of a liquid. This process produces a nearly monodispersed smoke. These machines are used to test U.S. Army masks, respirators, filters and other personnel protection equipment.

A description of the equipment is given elsewhere in this disclosure. The acceptable operation of the composition utilized in this invention has been confirmed by extensive testing in our research facility at Aberdeen Proving Ground, using the cited smoke penetrometers.

We have demonstrated that our invention, the method of use of the composition, not only meets U.S. Army test specifications, but we have found that the composition outperforms the historically "standard" material used in such testing.

Figure 1:
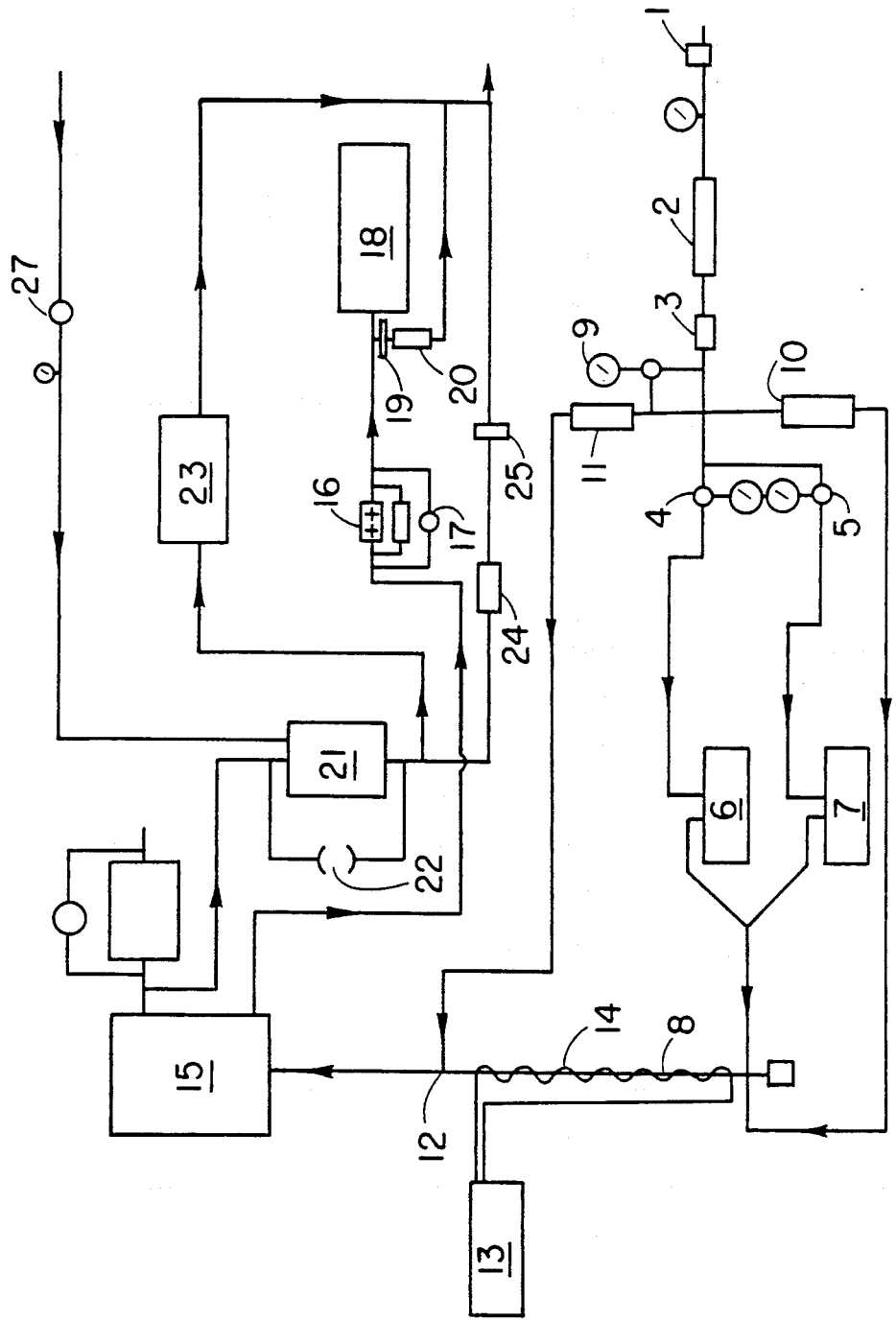
FIG. 1 is a diagram showing flow paths for aerosol generation, measurement, and filter test flows in the penetrometer.
Figure 2:
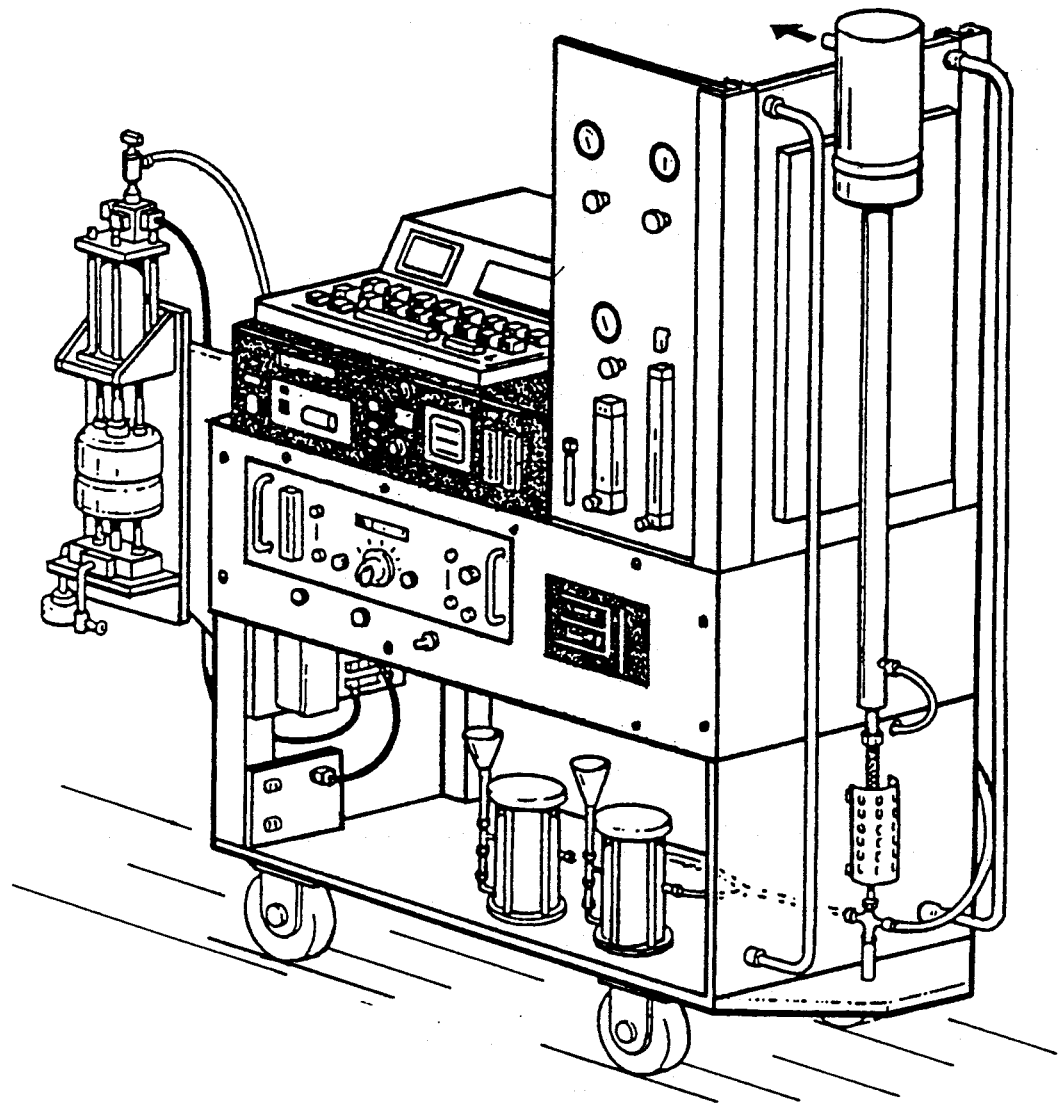
FIG. 2 is a sketch of the penetrometer with physical locations of the various system components, controls and indicators.

The composition and the method of use are described on the following pages. FIG. 1 shows schematically the flow diagram of the penetrometer machine. FIG. 2 shows an illustration of the same machine, with labels designating important components.

The discussion continues here with a background of our invention, followed by a system overview and a description of our system operation keyed to the numbers and labels shown on the figures. Finally, our method machine settings are tabulated to give the superior results claimed for the use of the composition in our method.

Referring to FIG. 1, the Los Alamos Monodispersed Aerosol Prototype Penetrometer was developed at the Los Alamos National Laboratory during a research program funded by the Product Assurance Directorate of the U.S. Army Armament, Munitions and Chemical Command. The purpose of the program was to design, build, and test a prototype respirator filter test penetrometer with improved performance, utilizing improved compositions. The improved penetrometer was to incorporate state-of-the-art principles, components, technology, and procedures for the task of testing respirator filters.

The specific design goals were:

to produce a stable test aerosol having a diameter of 0.2-0.3 m expressed either as the geometric mean diameter (GMD), or as the count mean diameter (CMD), and a geometric standard deviation (GSD) of 1.30 or less, and mass concentration $25 \pm 10$ mg/m$^3$.

to provide a reliable means of monitoring the size, distribution, and concentration of the test aerosol;

to produce a system capable of providing filter test flow rates of 16, 32, 42, 64, and 85 LPM;

to provide rapid response filter penetration measurements to the 0.03% level.

SYSTEM OVERVIEW

The Los Alamos generator utilizes a fine polydisperse aerosol to initiate production of a monodispersed aerosol. The polydisperse aerosol is produced by room temperature nebulization of our composition in a generator using a Laskin nozzle. This allows vaporization of small particles at temperatures below the material boiling point, decreasing the potential for thermal decomposition. In a parallel generator a aerosol is poduced from a diluted sodium chloride solution. This sodium chloride aerosol mixes with the composition aerosol stream which then enters the vaporization tube. The NaCl droplets dry to very small nuclei particles. The candidate material vapor is condensed by the addition of cooler diluting air while the NaCl aerosol provides a source of excess nuclei to initiate and control condensing candidate particle growth. By controlling the ratio of the composition's vapor to NaCl nuclei, a nearly monodispersed aerosol of particles in the submicron size range can be generated. The recondensed aerosol passes into an aging chamber to allow uniform mixing of the aerosol. From the aging chamber a sample of the aerosol is piped to a "LAS-X" laser aerosol spectrometer. The LAS-X is manufactured by Particle Measuring Systems, Inc., 1855 South 57th Court, Boulder, Colo. 80301. The LAS-X measures particle size frequency over a range of contiguous class intervals from which average particle size can be computed expressedas count mean diameter (CMD) and width of particle distribution, expressed as geometric standard deviation (GSD). Aerosol from the aging chamber is also piped to the filter test chuck for filter efficiency analysis. The chuck is a pneumatically-operated device which holds and seals the filter canister to be tested. Aerosol passing through the filter flows through a light scattering chamber upstream and down-stream of the filter to measure the percent of the original aerosol passing through the filter, i.e., the filter's efficiency.

SYSTEM OPERATION

Referring to FIG. 1, compressed house air for smoke generation enters the instrument through an electrically controlled solenoid valve (1, FIG. 1). The compressed air is regulated to 40 psi. before passing through a desiccant air dryer (2, FIG. 1). A 0.2 micron absolute HEPA filter removes any particulates from the air stream (3, FIG. 1). The a portion of the air stream flows to two regulators (4,5, FIG. 2) which control flows to the two aerosol generators (6,7, FIG. 1). Air streams from the two generators merge before entering the vaporization tube (8, FIG. 1).

After flowing through the HEPA filter (3, FIG. 1) compressed air is also supplied to a regulator which lowers the air pressure to 15 psi. (9, FIG. 1). The flow separates into two air streams, the bypass air and the dilution or quench air. The rate of flow of the bypass air is controlled by a flowmeter (10, FIG. 1) and is adjustable from 0-25 LPM. The bypass air enters the vaporization tube opposite the outlet from the aerosol generators. The primary function of the bypass air is to cool the vaporation tube while no aerosol is being generated; it also serves to dilute and increase aerosol flow through the vaporization tube. The dilution air flow-meter (11, FIG. 1) controls the flow of the dilution air, flow may be varied between 0-100 LPM. The dilution air merges with the vaporized aerosol just after leaving the vaporization tube. The dilution air controls the rate of condensation and concentration of the aerosol.

A thermocouple (12, FIG. 1) monitors the temperature of the aerosol in the vaporization tube. An Omega 4000 series temperature controller (13, FIG. 1) displays the vaporation tube temperature while controlling voltage output to electric heat tape (14, FIG. 1) which is employed to heat the vaporization tube. Temperature of the aerosol can be controlled from 25°-200° C.

From the vaporization tube the aerosol flows to an aging chamber (15, FIG. 1) where recondensation and uniform mixing is accomplished. A small fraction of the candidate material smoke is drawn from the outlet of the aging chamber through a in-line capillary dilution system (16, FIG. 1). A magnehelic gauge (17, FIG. 1) indicates the pressure differential across the dilution system. The LAS-X laser aerosol spectrometer samples the diluted smoke, and sends the data to the Hewlett Packard Microcomputer (18, FIG. 1) which then performs the analysis and prints the results. This system measures and prints smoke GMD and GSD. Smoke from the capillary diluter that is not used by the LAS-X is filtered via a in-line HEPA filter (19, FIG. 1). Flow of sample smoke is controlled by the sample control value (20, FIG. 1). Sample air is then exhausted via the house vacuum source.

Compressed air for operation of the chuck is controlled by a pressure regulator (27, FIG. 1) set to 30 psi. Smoke for filter testing is drawn from the aging chamber through the chuck (21, FIG. 1). Filter resistance is measured by a magnehelic gauge (22, FIG. 1). Smoke concentration penetrating the test filter is measured downstream of the test chuck by a light scattering photometer (23, FIG. 1). The photometer indicates percent penetration through the test filter. Smoke remaining in the sample flow is filtered by a in-line HEPA filter within the photometer. Smoke remaining in the test air is removed by an in-line HEPA filter (24, FIG. 1). Test air flow is controlled by a flowmeter (25, FIG. 1). Test air is exhausted via a house vacuum source. Smoke generated which is not used for filter testing is cleared of particulate by a HEPA filter (26, FIG. 1).

RECOMMENDED MACHINE SETTINGS

The following machine parameters were found in our method to produce an aerosol, using our candidate material, which gave the same or better test smoke performance as those measured experimentally using the standard composition which is carcinogenic. Actual settings may differ slightly between machines.

| | |
|---|---|
| Our composition nebulization pressure (5. FIG. 1) | 2.0 psi |
| NaCl nebulization Pressure (4, FIG. 1) | 4.0 psi |
| Vaporization tube temperature (13, FIG. 1) | 170 C |
| Aerosol dilution air flow (11, FIG. 1) | 25 LPM |
| Bypass air (10, FIG. 1) | 0 LPM |

The machine settings above were found to produce a mass concentrations of approximately 23 mg/m$^3$, GMDs of 0.20 micrometers with GSDs of approximately 1.25. These specifications met or exceeded those obtained using dioctyl phthalate, and were within the U.S. Army test requirements of 0.18-0.33 $\mu$m GMD and GSD less or equal to 1.30. To obtain higher concentrations, the candidate material and NaCl nebulization pressures were raised.

AEROSOL MEASUREMENTS

This information is provided (1) to clarify how aerosol particle size distributions are represented, (2) to give U.S. Army smoke aerosol specifications for filter-testing penetrometer machines used to test respirators and mask canisters, and (3) to compare typical performance obtained using dioctyl phthalate in our penetrometer machine with that obtained by us using the present composition or mixture in a penetrometer machine using the method as described herein.

The U.S. Army requires these test smokes (aerosols) to meet these specifications:

(1) The geometric mean diameter (GMD), in micrometers ($\mu$m), of the aerosol must lie between 0.18 $\mu$m and 0.33 $\mu$m. This is the count or number mean of the distribution. That is, all particles in all size ranges are counted, and a distribution is drawn showing the total number of particles in all ranges (a histogram). From this, a mean size is determined.

(2) The geometric standard deviation (GSD) of the distribution must not exceed 1.30. The GSD is a measure of the narrowness (width) or "monodispersity" of the particle size distribution. An aerosol of particles of all one size would have a GSD=1.00. This is impossible to achieve even with latex spheres that are used to calibrate the instruments. The specified upper limit of GSD=1.30 insures that the width of the distribution is adequately narrow for desired tests. By comparison, aerosols produced by spraying (without vaporization and recondensation) often have GSDs of 2.00 or more.

(3) The smoke concentration at the test chuck where filter canisters are inserted must be 25 mg/m$^3$ plus or minus 10 mg/m$^3$. Concentrations that are too high can be reduced by process control adjustments.

In conclusion, the improved method of testing the efficiency of a particulate protective filter utilizing the aerosol as described herein, has been shown. The specific point of action or invention in the described machine, system, and method is the penetration of the filter.

What is claimed is:

1. In an improved method of testing a particulate filter, the improvement consisting essentially of passing a salt nucleus coated with a dispersed aerosolized composition through said filter, said composition containing about 97-99% by volume of a poly-alpha olefin having a chain length of 20 carbon atoms and about 1-3% by volume of a poly-alpha olefin having a chain length of 30 carbon atoms.

2. The method of claim 1 wherein the geometric mean diameter in micrometers of said aerosol lies between about 0.18 and 0.33.

3. The method of claim 2 wherein the geometric standard deviation of said mean diameter must be below about 1.30.

4. The method of claim 3 wherein the concentration of said aerosol must be 25 mg/m$^3$ plus or minus 10 mg/m$^3$.

* * * * *